US006203683B1

(12) United States Patent
Austin et al.

(10) Patent No.: US 6,203,683 B1
(45) Date of Patent: Mar. 20, 2001

(54) ELECTRODYNAMICALLY FOCUSED THERMAL CYCLING DEVICE

(75) Inventors: Robert H. Austin; Edward C. Cox; Chia-Fu Chou, all of Princeton, NJ (US)

(73) Assignee: Princeton University, Princeton, NJ (US)

( * ) Notice: Subject to any disclaimer, the term of this patent is extended or adjusted under 35 U.S.C. 154(b) by 0 days.

(21) Appl. No.: 09/188,284

(22) Filed: Nov. 9, 1998

(51) Int. Cl.⁷ .................................................. G01N 27/26
(52) U.S. Cl. ........................................ 204/547; 204/643
(58) Field of Search .................................... 204/643, 547

(56) References Cited

U.S. PATENT DOCUMENTS

| 5,427,663 | 6/1995 | Austin et al. ........................ 204/549 |
| 5,605,662 | 2/1997 | Heller et al. ........................ 422/68.1 |
| 5,800,690 | 9/1998 | Chow et al. ......................... 204/451 |

OTHER PUBLICATIONS

Kheterpal, et al., "Design and Synthesis of fluorescence energy transfer dye–labeled primers and their application for DNA sequencing and analysis", Oct. 1995, 231(1); pp. 131–140.

Brody, et al., "Biotechnology at Low Reynolds Numbers", Biophysical Journal, vol. 71, Dec. 1996, pp. 3430–3441.

Asbury et al., "Trapping of DNA in Nonuniform Oscillating Electric Fields", Biophysical Journal, vol. 74, Feb. 1998, pp. 1024–1030.

Washizu et al., "Applications of Electrostatic Stretch–and–Positioning of DNA," IEEE Transactions on Industry Applications, vol. 31, No. 3, May/Jun. 1995, pp. 447–455.

Washizu et al., "Electrostatic Manipulation of DNA in Microfabricated Structures", IEEE Transactions on Industry Applications, vol. 26, No. 6, Nov./Dec. 1990, pp. 1165–1172.

Duke et al., "Pulsed–field electrophoresis in microlithographic arrays", Electrophoresis 1996, vol. 17, pp. 1075–1079.

Bakajin et al., "Electrohydrodynamic Stretching of DNA in Confined Environments", PRL, Mar. 1998, pp. 2737–2740.

Carlson et al., "Self–Sorting of White Blood Cells in a Lattice", Physical Review Letters, Sep. 1997, vol. 79, No. 11, pp. 2149–2152.

Wilding, "PCR in a silicon microstructure", Clinical Chemistry, 40(9), Sep. 1994, pp. 1815–1818 (Abstract Only).

*Primary Examiner*—Jill Warden
*Assistant Examiner*—Alex Noguerola
(74) *Attorney, Agent, or Firm*—Venable; Michael A. Gollin

(57) ABSTRACT

A device for the integrated micromanipulation, amplification, and analysis of polyelectrolytes such as DNA comprises a microchip which contains electrodes for dielectrophoresis powered by an AC signal generator, and a trapping electrode attached to a direct current source that can be heated to specific temperatures. Nucleic acids can be heated and cooled to allow for denaturation, the annealing of complementary primers and enzymatic reactions, as in a thermocycling reaction. After such a reaction has been completed on the trapping electrode, the dielectrophoretic field can be switched to a direct current to release the product and direct it through a matrix for fractionation and/or analysis. The device includes data analysis equipment for the control of these operations, and imaging equipment for the analysis of the products. The invention permits the efficient handling of minute samples in large numbers, since reactions occur while sample material is positioned on an electrode in a microfluidic channel. Because the positioning, reactions, and release into a fractioning matrix are all integrated from the focusing wire, the need to transfer samples into different tubes is eliminated, thus increasing the efficiency and decreasing the possibility of damage to the samples.

28 Claims, 5 Drawing Sheets

ELECTRODYNAMICALLY FOCUSED THERMAL CYCLING DEVICE

BACKGROUND OF THE INVENTION

The invention relates to a device for thermocycling polyelectrolytes, in particular for amplification of nucleic acids. Specifically, the invention involves trapping minute amounts of nucleic acids in a microfabricated, dielectrically focused device, thermocycling them, and releasing them for fractionation or analysis.

The amplification of nucleic acids is central to the current field of molecular biology. Library screening, cloning, forensic analysis, genetic disease screening and other increasingly powerful techniques rely on the amplification of extremely small amounts of nucleic acids. As these techniques are reduced to a smaller scale for individual samples, the number of different samples that can be processed automatically in one assay expands dramatically. For further improvements, new integrated approaches for the handling and assaying of a large number of small samples are needed.

With the polymerase chain reaction (PCR) for nucleic acid amplification, a purified DNA polymerase enzyme is used to replicate the sample DNA in vitro. This system uses a set of at least two primers complementary to each strand of the sample nucleic acid template. Initially, the sample nucleic acid is heated to cause denaturation to single strands, followed by annealing of the primers to the single strands, at a lower temperature. The temperature is then adjusted to allow for extension of the primers by the polymerase along the template, thus replicating the strands. Subsequent thermal cycles repeat the denaturing, annealing and extending steps, which results in an exponential accumulation of replicated nucleic acid products.

PCR represents a considerable time savings over the replication of plasmid DNA in bacteria, but it still requires several hours. PCR also has limitations in the subsequent handling of the product. Most reactions occur isolated in a test tube or plate containing the required reagents. Further analysis of these products entails removing them from the tube and aliquoting to a new environment. Significant delay and loss and damage to the product may result from such a transfer. Emerging technology in the display of nucleic acids in arrays on chips, for further identification and selection, requires a more precise method of transfer of samples from amplification step to chip than is possible by dispensing the contents of each reaction tube individually.

Another disadvantage of PCR is the requirement of a reaction tube which has a volume possibly too large for the amplification of particularly minute amounts of starting template and other reagents. PCR is able to amplify just one molecule of template, but the volume of the reaction mixture makes this goal difficult to achieve. The nature of the reaction tube also requires a significant volume of the other reagents. Conventional PCR involves heating and cooling the reaction tube several times for each cycle, requiring elaborate instrumentation to control the temperature of the apparatus which holds the tubes, and the tubes and solutions they contain, over time.

Lab-on-a-chip or biochip technology for manipulating DNA on a small scale is a recent development in the art. For example, Austin et al., U.S. Pat. No. 5,427,663, describes a microlithographic array for fractionating macromolecules. Heller, U.S. Pat. No. 5,605,662 describes a microfabricated device having DC microelectrodes for DNA hybridization. Individual wires in a direct electrophoretic field have been used to focus and launch DNA into separation media.

Microfabricated devices can be used for PCR. Wilding, et al. (Clin.Chem. 40:1815–8, 1994) designed a photolithographed, sealed silicon chip which can receive reagents by capillary action and can be mounted on a Peltier heater-cooler. This design reduces reagent volumes, but requires an external source for heating and does not couple positioning and manipulation of the nucleic acids, and so amplification and subsequent analysis on a fractionation matrix cannot be achieved without transfer of samples. Thus, prior art systems for the amplification of nucleic acids do not integrate micromanipulation and amplification steps, such that the need for transfer steps reduces the quantity and quality of the products, and time and labor are increased.

In another field, dielectrophoresis has been used to position cells and molecules on a micron scale. Washizu and Kurosawa, IEEE Transactions on Industry Applications, 26 (6): 1165–1172, 1990, and Washizu et al., IEEE Transactions and Industry Application, 31(3):447–455, 1995, used high voltage ($10^4$ V/cm) and high frequency (1 MHz) alternating currents to generate a dielectric field in a micron-sized floating electrode. Alignment, permanent fixation, stretching, and cutting of DNA molecules was described. Asbury and van den Engh (Biophys. J. 74:1024–30, 1998) report a sealed device having an array of 100 strips of gold which, when placed in an oscillating field, reversibly traps DNA along the edges of the strips. These papers did not demonstrate fractionation of DNAs, and do not suggest dielectric trapping in a thermal cycling device for DNA amplification. Such devices are unsuitable for complex enzymatic reactions, such as PCR, which require precise temperature control, and do not provide microfluidic structures that can be used for transfer to a fractionating medium without damage. Moreover, as the Takashima group claimed in the 1970s, the dielectric constant of single stranded DNA is less than double stranded DNA which would discourage use of dielectrophoresis for single stranded uses such as PCR.

SUMMARY OF THE INVENTION

A device for the integrated micromanipulation, amplification, and analysis of polyelectrolytes such as DNA comprises a microchip which contains electrodes for dielectrophoresis powered by an alternating current signal generator, and a trapping electrode attached to a current source that can be heated to specific temperatures. Nucleic acids can be heated and cooled to allow for denaturation, and the annealing of complementary primers and enzymatic reactions, as in a thermocycling reaction. After such a reaction has been completed on the trapping electrode, the dielectrophoretic field can be switched to a direct field to release the product and direct it through a matrix for fractionation. The device includes data analysis equipment for the control of these operations, and imaging equipment for the analysis of the products. The invention permits the efficient handling of minute samples in large numbers, since reactions occur while sample material is positioned on an electrode in a microfluidic channel. Because the positioning, reactions, and release into a fractioning matrix all occur at the trapping electrode, which serves as a focusing wire, the need to transfer samples into different tubes is eliminated, thus increasing the efficiency and decreasing the possibility of damage to the samples.

This invention relates to a microfluidic device for trapping nucleic acids on an electrode by dielectrophoresis, thermocycling them on the electrode, and then releasing them and fractionating through a gel, or other medium, for analysis. The invention avoids the need for an external thermocycling device, reduces the volume and amount of starting materials and reagents, and reduces the time and manipulations needed to complete an amplification protocol and sequencing.

This arrangement improves prior nucleic acid amplification steps by decreasing the required time and reagent volume. Positioning the template on an electrode reduces the volume of the reaction down to a volume proportional to the narrow surface of the electrode and the microchannel spanning the electrode. The entire apparatus is contained on a monolithographic wafer. Because the reactions take place in such a small volume, and the nucleic acid templates are positioned directly on the actual heat source, as opposed to in a tube isolated from the heat source, the time for temperature changes to perform PCR is significantly reduced.

The use of an integrated device for dielectric focusing, to position the macromolecule templates for amplification and for subsequent analytical steps such as fractionation by size or sequencing, eliminates the need for transferring samples between these steps. When the samples are released from the positioning electrode, they can be electrophoresed through an adjacent matrix to achieve fractionation. These coupled reactions are suitable for multisample arrays, such as standard plates which are multiples of 96-sample arrangements.

This invention comes as a breakthrough in the crowded and heavily researched field of nucleic acid amplification. It succeeds where many previous efforts at integrating nucleic acid amplification and fractionation have failed.

This invention runs contrary to the direction of the prior art, which requires extrinsic thermal control. This invention provides for thermocycling with an intrinsic rather than extrinsic heat source and temperature measurement, thus solving a problem previously thought to be insoluble. The invention omits the need for an extrinsic heat source and temperature-sensor, an element required in prior art methods, without loss of ability.

The inventive device differs from the prior art in modifications which were not previously known or suggested, such as using dielectrophoresis to reversibly trap a polyelectrolyte, and using the trapping electrode as a heater and in-situ temperature sensor. The invention thereby provides advantages that were not previously appreciated, as described above.

This invention satisfies a long felt need for an integrated microfabricated device suitable for thermocycling of polyectrolytes using minimal starting materials, in a minute volume, and permits amplification and fractionation of DNA without transfer.

The dimensions of the trapping electrode are important to obtaining the advantages of the invention and depend on the size of the microfluidic channel. The exposed length of the electrode is preferably the width of the channel, although a smaller portion could be exposed to provide for particular focusing effects. The total length may be about 2 cm with contact pads at the ends. The exposed electrode length is typically the width of the channel but need not be more than a dot. The electrode width (in the dimension parallel to the channel) can be from about 10 nm to about 20 $\mu$m, preferably from about 1 to about 10, for example 10 $\mu$m. The width depends on manufacturing techniques and the desired loading of the wire. The height of the trapping electrode from the channel floor is generally much less than the electrode width, and depends in part on the manufacturing process, and can be from about 10 to about 100 nm, preferably about 100 nm (0.1 $\mu$m). The trapping electrode can be made of any suitable material that serves as a floating electrode for dielectrophoresis, that can reversibly trap polyelectrolytes, is chemically inert and is a resistive heater, preferably one which has predictable temperature/resistance characteristics. Platinum is particularly preferred. In other embodiments the trapping electrode can be made of nickel, gold, tungsten or iridium. By far, platinum is the most favorable due to its linearity with temperature and inertness.

The trapping electrode is preferably positioned essentially perpendicular to the microchannels. If the trapping electrode is positioned at an angle to the channels, it may induce DNA drifting along the trapper electrode and cause nonuniform releasing. The arrangement should be able to release the sample uniformly.

The dimensions of the field electrodes are not as critical as that of the trapping electrode, so long as the field electrodes produce the desired dielectrophoretic field at the trapping electrode. Conventional gold electrodes may be used, as can other metals having the desired characteristics of inertness with respect to electrolysis of the electrode. The length of the field electrodes is preferably at least slightly greater than the width of the channel, or the sum of the widths of the multiple channels, to span multiple channels with collector electrodes, which may be as wide as about 10 cm for a large device. The width or thickness of the electrodes can be in the range of about 100 $\mu$m to about 1 mm, preferably from about 200 $\mu$m to about 500 $\mu$m, for example 250 $\mu$m. The gap between the electrodes is at least slightly larger than the length of the microfluidic channel in which the trapping electrode is located.

The field strength generated between the field electrodes is selected to optimize speed of focusing and/or separation depending on the channel height. Although higher field strengths cause problems in prior art arrangements, field strengths here could be as high about 10,000 V/cm. Field strengths of 30–60 V/cm up to 1,000 V/cm or higher have been shown to be suitable. The trapping frequency can be from about 1 to about 1 MHz, preferably from about 100 Hz to about 500 Hz. The ac voltage when the sample is released can be as high as about 1000V, and is preferably below about 200V, most preferably zero volts. The frequency is not critical for releasing but the voltage between field electrodes is because it must be consistent with fractionation and transport requirements.

The dimensions of the microchannel depend on the electrode dimensions and the number of channels. The length may be as desired depending on the physical layout of the chip, and may be from about 1 to about 10 cm, preferably from about 2 to about 4 cm, for example about 3 cm. The width of the microchannel may be from about 1 $\mu$m to about 1 mm, preferably from about 50 to about 500 $\mu$m, preferably about 500 $\mu$m. The height of the microchannel may be from about 0.1 $\mu$m to about 100 $\mu$m, preferably from about 1 to about 10 $\mu$m depending on the voltage but higher heights may cause heating. The number of microchannels can be up to about 200 for example, with a total width of 5–10 cm, or more as desired, depending on manufacturing technologies.

The substrate chip is typically quartz or silicon dioxide, for ease of manufacture and transparency suitable for microscopic examination, but other materials and composites now known or later discovered could be used, for example glass, silicon nitride, or polymers. The supports defining the walls of the microchannels may be silicon dioxide, polyimide, PMMA or other suitable inert materials that can be deposited with the requisite accuracy.

The cover for the microchannels may be glass, quartz, polymers or other suitable material, preferably transparent at least in the regions where observation of the microchannels is required. The cover may be integral or removable, depending primarily on the manufacturing process.

In the most preferred embodiment, the polyelectrolyte is DNA, while in other embodiments it might be a protein, or other biological or synthetic polymer. With DNA, the buffer solution preferably contains suitable salts and buffers, such as 1/2X TBE, TAE, MOPS, SDS/Tris/glycine, or TAPS.

For microreactions with polyelectrolytes other than nucleic acids, the material can be trapped on the trapping electrode by dielectrophoresis, subjected to desirable microreactions, including thermal cycling as needed, and then released and fractionated. For example, a polymerase protein may be focused and trapped together with nucleic acid to facilitate polymerization.

In summary, the invention relates to a device for selectively trapping, thermocycling, and releasing polyelectrolytes, comprising: (a) a microlithographic substrate having a microfluidic channel dimensioned to accommodate a fluid, (b) field electrodes positioned to provide a dielectrophoretic field along the channel in response to an alternating current, (c) a trapping electrode positioned between the field electrodes across the channel, the field electrodes and trapping electrode being capable of fluid communication with each other via the channel, and (d) circuitry controlling current to the field electrodes and trapping electrode, whereby a polyelectrolyte in solution may be (i) trapped on the trapping electrode when a trapping alternating field is applied to the field electrodes, (ii) heated when a field is applied to the trapping electrode and (iii) released when the trapping alternating field is not applied.

The device may comprise a matrix in the channel capable of fractionating polyelectrolytes released from the collecting electrode, and imaging equipment to visualize the polyelectrolytes. There may be a plurality of parallel channels arranged on the substrate, which may be $SiO_2$ polyimide, p-xylylene or PMMA (polymethyl methacryate) or other suitable material. The channel may be covered with a seal comprising a coverslip and a sealant gasket.

A method for thermal cycling of a polyelectrolyte comprises: (a) placing the polyelectrolyte in solution in a channel having a trapping electrode, (b) trapping the polyelectrolyte on the trapping electrode by applying a dielectrophoretic field to the solution, and (c) releasing the polyelectrolyte by removing the dielectrophoretic field, and further heating the polyelectrolyte by applying a current to the trapping electrode, and removing the current and allowing the nucleic acid to renature. The polyelectrolyte may be nucleic acid, denatured on heating.

The method may further comprise determining the sequence of the nucleic acid by reacting the trapped nucleic acid with amplification reagents, allowing nucleic acid amplification to occur, releasing the polyelectrolyte by removing the dielectrophoretic field, fractionating the nucleic acid, and scanning the fractions. A plurality of samples can be processed simultaneously in separate channels. The method can include fractionating and/or analyzing the released polyelectrolyte by electrophoresis such as in a field produced by the field electrodes.

BRIEF DESCRIPTION OF THE DRAWINGS

The invention is better understood by reading the following detailed description with reference to the accompanying figures, in which like reference numerals refer to like elements throughout, and in which:

FIG. 6 shows the effect of trapping by altering the frequency of alternating field.

DETAILED DESCRIPTION OF THE PREFERRED EMBODIMENTS

Figure 1:
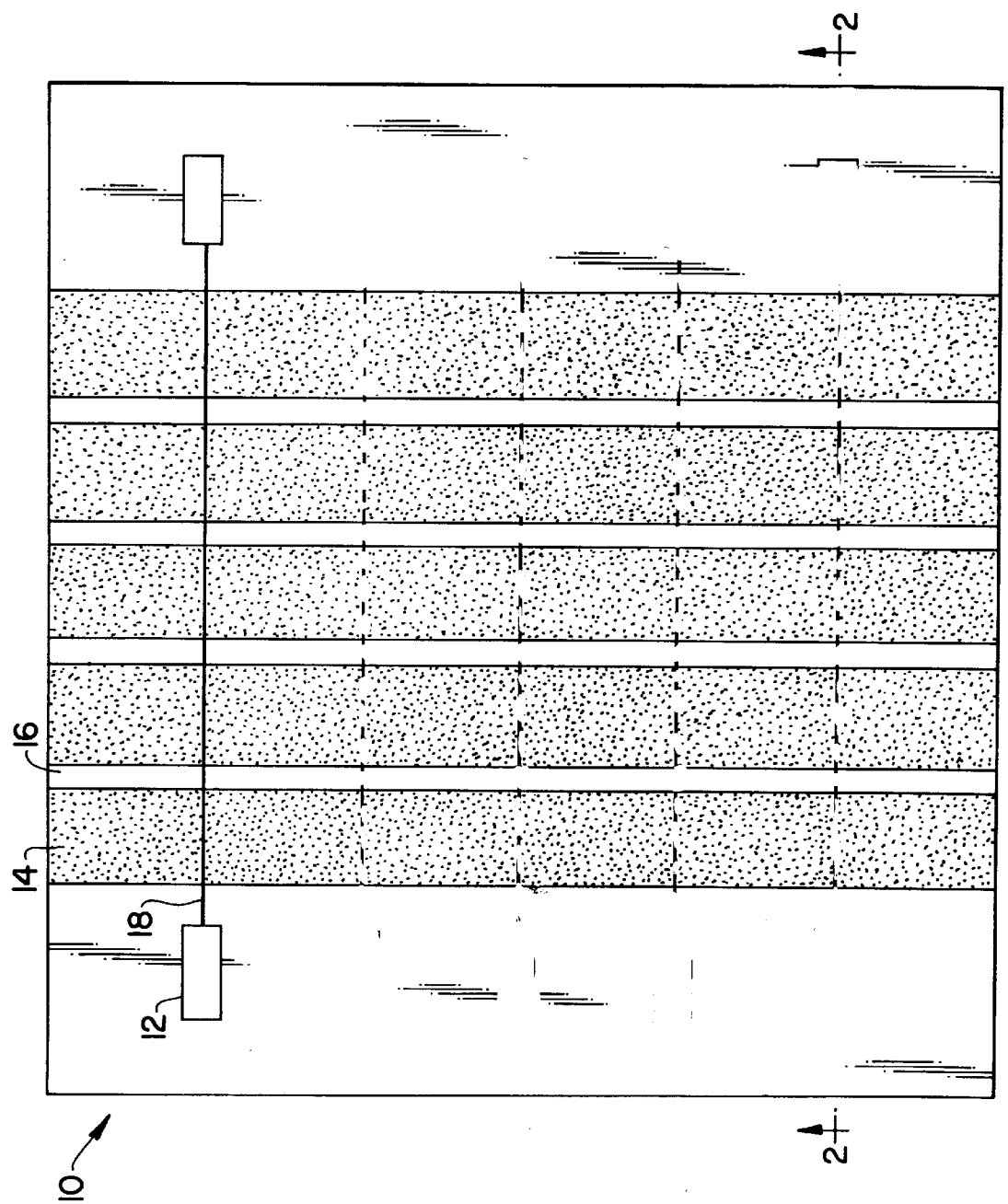
FIG. 1 is a schematic layout of electronic circuits of the device not to scale.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose. Each reference cited herein is incorporated herein by reference in its entirety as if individually incorporated by reference. The terms used herein are intended to have their conventional meaning as understood by a person of ordinary skill, as supplemented by particular definitions provided here.

Dielectrophoresis, generally, means the translational motion of polarizable neutral matter in a nonuniform electric field. The term dielectrophoretic field refers to the nonuniform field which causes polarization and thus dielectrophoresis. See Pohl, Dielectrophoresis (Cambridge Univ. Press, 1978).

Thermal cycling refers to a protocol of discrete temperature incubation periods which are repeated in a succession of cycles. These protocols may also include other periods of specific temperature incubations which are not cycled. Thermocycling usually involves repeated polymerization of single stranded nucleic acids in order to amplify the amount of original nucleic acid.

The term polyelectrolytes refers to biological or synthetic polymeric molecules, often linear, with multiple ionic groups that are charged at a particular pH or in an electric field, and become dipoles susceptible to manipulation in a dielectrophoretic field.

Alternating current means a current that alternates cyclically at a particular frequency, with a baseline that may be zero volts or a particular voltage.

Microfluidic means the physics and engineering principles that apply to fluids moving on a microscopic scale.

The term matrix refers to any suitable material such as a gel used for fractioning macromolecules, usually according to their size but may also include fractionation by electronic change and separation based on affinity such as ligand binding.

The terms DNA and nucleic acid are used broadly to encompass genomic DNA, cDNA, mRNA, mt DNA, tRNA, and rRNA, oligonucleotides, and single, double, and triple stranded molecules. Genomic DNA is the form found in the nucleus of the cell and includes non-transcribed sequences. cDNA is formed by reverse transcription of expressed mRNAs. mRNA is the product of transcription of the genomic DNA of expressed genes. mtDNA is found within the mitochondria. tRNA is transfer RNA, used in translation. rRNA is found at the ribosomes.

FIG. 1 shows an embodiment of the invention, an apparatus for dielectrophoresis on an electrode of platinum wire. Wire 18, deposited on quartz chip 10, extends between contact pads 12 and spans open channel 16, generally perpendicular to the channel. The open channel 16 is formed between support substance 14 made e.g. of silicon dioxide, polyimide, or PMMA. Multiple channels 16 can be formed by the arrangement of these supports 14 in parallel rows. The multiple open-channels 16 and crossing wire 18 are arranged as desired on substrate chip 10. To facilitate fabrication, a plurality of identical wires parallel to 18 may be deposited on the substrate and then after selection of the floating electrode 18, the others are scored to eliminate them from the channel.

The use of a single trapping electrode permits focusing and separation in an essentially two-dimensional microfluidic environment, exhibiting confinement effects. An array of one or more additional trapping electrodes could be implemented downstream to refocus or otherwise re-treat the polyelectrolyte. Channel height and width are important parameters. Beneficial effects result from use of a trapping electrode in a microfluidic channel as opposed to a wide array such as e.g. in Asbury and van den Engh. Polyelectrolyte loading is a function of the channel height and width, the height of the wire, and the size and nature of the polyelectrolyte (e.g., RNA vs. DNA). The channel width may preferably be somewhere in the range of about double the Gaussian coil size of the DNA or polyelectrolyte, and about twice as wide as high.

Figure 2:
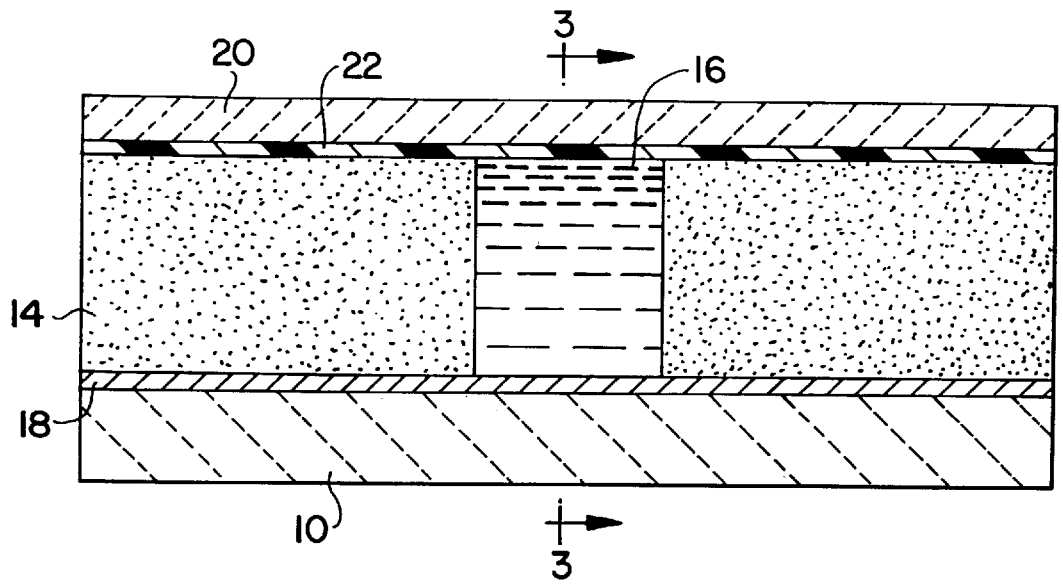
FIG. 2 is a cross-sectional end view of a sealed chip seen from one end of a capillary channel.

FIG. 2 shows a cross-sectional end view of a sealed channel at the position of wire 18 as shown for one example of the invention. Substrate 10 forms the base along which the wire has been deposited. Supports 14 extend vertically with a gap between them, forming an open channel 16, the channel being approximately 1 $\mu$m in height and 0.5 mm in width. The channel is sealed on top with a coverslip 20 and a gasket seal 22 of PDMS (e.g. General Electric RTV 615). In prior devices, the seals also served to define the gaps and were inadequate to provide a well-defined depth and uniformity on a microscopic scale. Washizu and Kurosawa used resin and Asbury and Van den Engh used agarose. The use of protolithograpy to define the gap is a superior approach. The sealing technique using an RTV-coated coverslide or equivalent structure permits washing and reuse, although in practice a disposable arrangement may be preferable.

Figure 3:
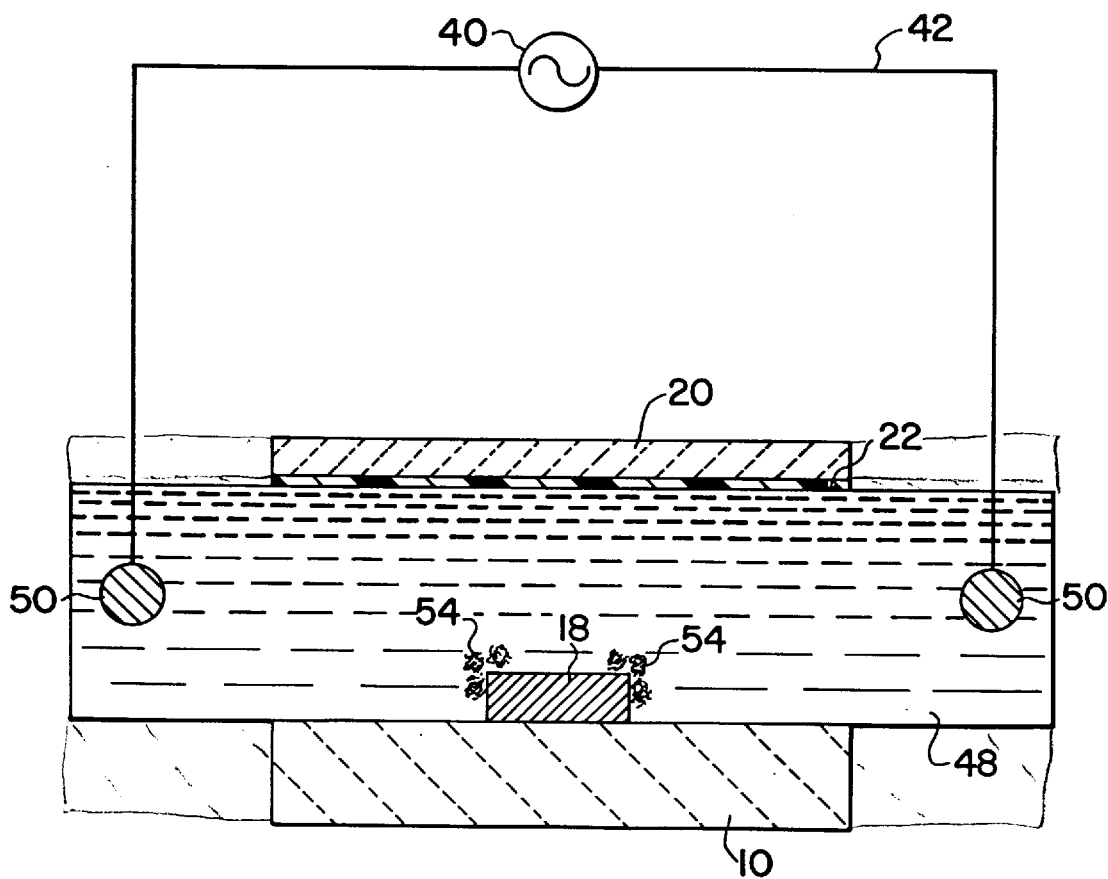
FIG. 3 is a cross-sectional side view (not to scale) of a sealed chip seen at the point of a platinum wire showing circuitry to apply an AC field for dielectrophoresis.

FIG. 3 shows a cross sectional side view of the sealed chip along the axis of the trapping wire. Again, substrate 10 is shown on the bottom, upon which wire 18 rests. An alternating current (ac) signal generator 40 is attached by wires 42 to electrodes 50 of gold or other suitable material, to produce the dielectrophoresis which positions the nucleic acid 54. The channel is sealed with a coverslip 20 and a seal of PDMS coating 22. A buffer 48 fills the channel. Another approach is to make a negative pattern of the channels, e.g., of FIG. 2 by photolithography, then to make a positive cast of the channel from PDMS, then to deposit the electrode on the ceiling coverslide. This arrangement provides identical dielectrophoretic effects.

Figure 4:
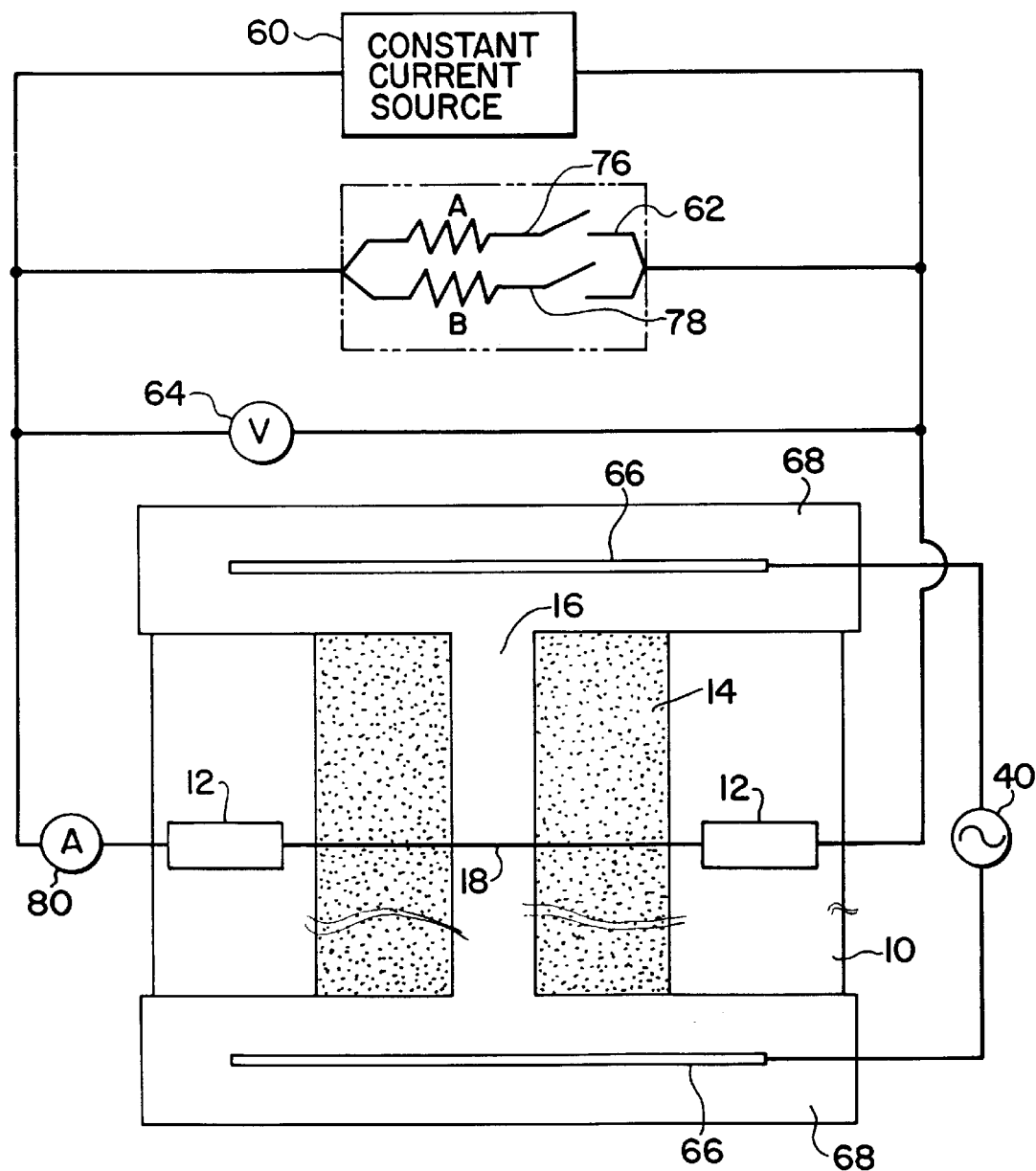
FIG. 4 is a layout of a nucleic acid amplification microchip suitable for multiple-channel operation.

In FIG. 4 a layout of the electronic circuit is shown. Again, supports 14 on chip 10 form a channel 16 which is crossed by a wire 18 ending in pads 12. The pads 12 are attached to an ampmeter 80 and a voltmeter 64. In parallel to the voltmeter, wire 18 is also attached to a resistor box 62 containing two resistors A 76 and B 78. A constant current source 60 is also connected in parallel. To provide dielectrophoretic focusing at trapping electrode 18, an AC generator 40 is connected to two field electrodes 66 running parallel to the trapping wire 18. The field electrodes are each in buffer baths 68 in fluid communication with channel 16.

Thermal cycling is preferably accomplished by means of the trapping wire, but could alternatively employ auxiliary heating and/or cooling such as a Peltier device beneath the trapping assembly. Heating could also be achieved by magnetic flux induced current through the Pt wire or by infrared light sources shining directly on the chip.

Figure 5:
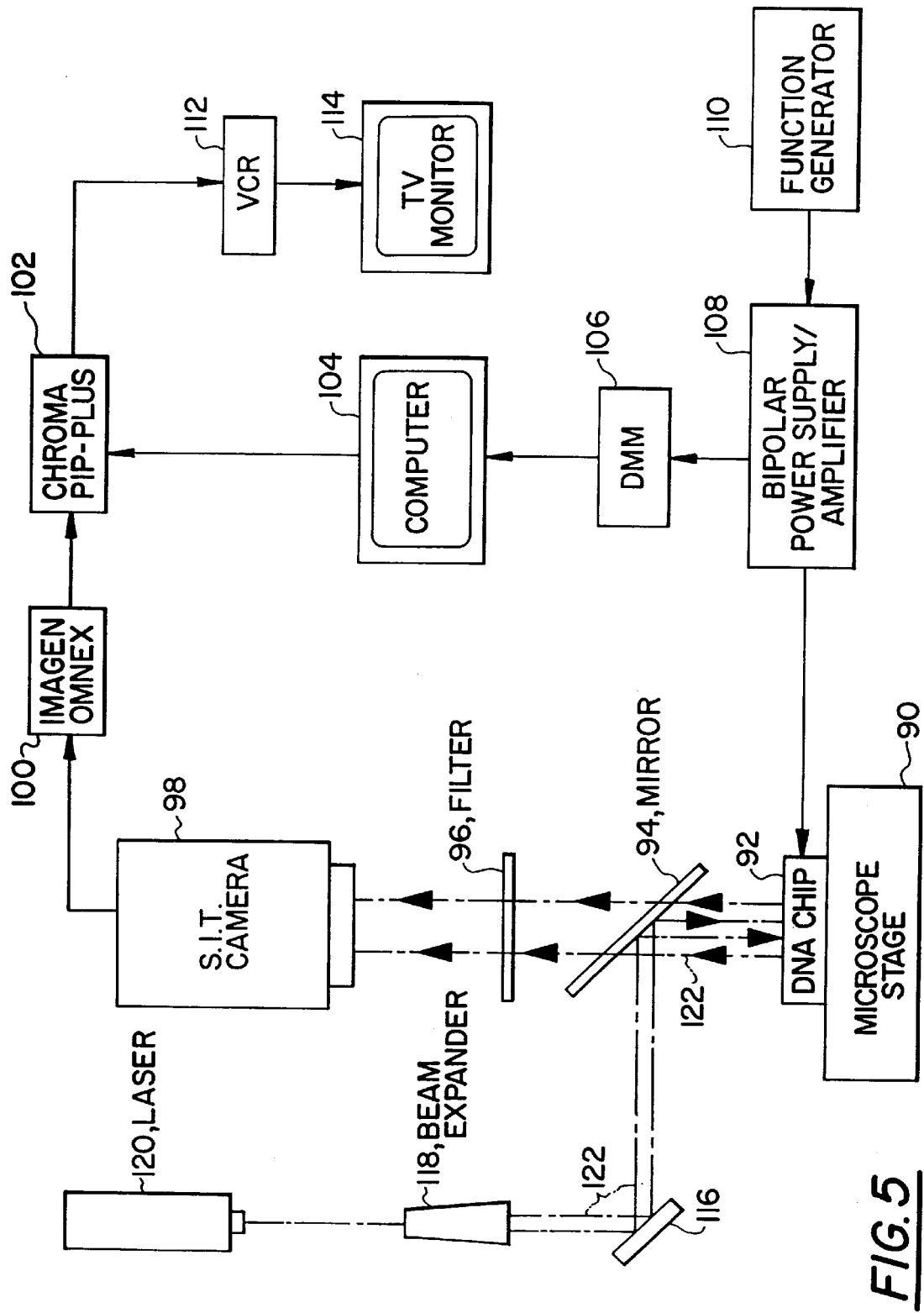
FIG. 5 shows an experimental setup for operating and monitoring the device.

In FIG. 5, an experimental setup as used in the examples is depicted. DNA chip 92 rests on a microscope stage 90. A laser beam with a wavelength of 488 nm is emitted from an Ar+-laser 120 and is passed through a beam expander 118 and reflected off mirror 116 and dichroic mirror 94 to the DNA chip 92. Reflections of this light pass back through the dichroic mirror 94 and through a 500–560 nm band-pass filter 96 where they are captured by a silicone intensified target (S.I.T.) camera 98. The image is then transfered to an image processor 100 (Imagen Omnex) and into a Picture-in-Picture display device 102 (Chroma PIP-Plus). The current at the DNA chip is controlled by function generator 110 (e.g. HP 3325A) and a bipolar power supply/amplifier 108 (KEPCO BOP 1000M). Information from the electronic circuit passes from power supply/amplifier 108, through a digital multimeter 106 (HP34401A) and computer 104 (IEEE488 with Lab View readout of frequency, Vac, and Vdc) and into the Chroma PIP-Plus 102. The signal goes out of the Chroma PIP-Plus to a VCR 112 and TV monitor 114. Many of these components would be unnecessary in a commercial design, for example, the camera, the microscope, and the laser, for example using near field optical techniques and light emitting diodes, waveguides or other chip-integrated systems.

Figure 6A:
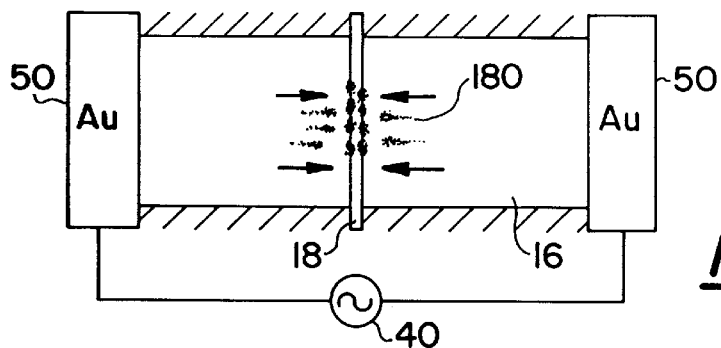
FIG. 6A shows strong trapping and FIG. 6B shows weak trapping of DNA.
Figure 6B:
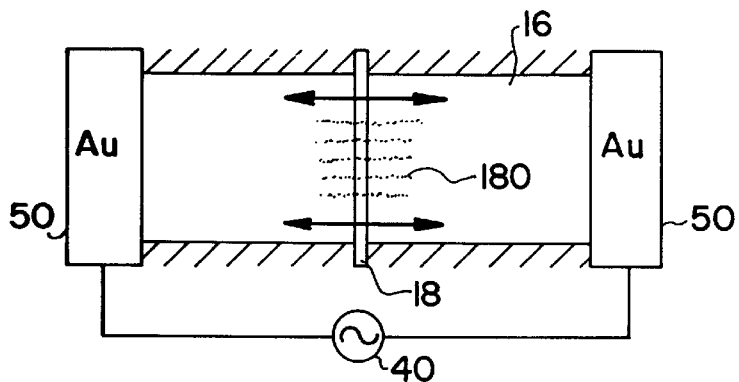

FIG. 6 shows a cartoon demonstration of trapping and releasing DNA. In FIG. 6A, the field conditions are f=100 Hz, Eac=30 V/cm, and Edc=0 V/cm. T4 DNA 180 is shown migrating to trapping electrode 18 under influence of the dielectrophoretic field. In FIG. 6A, the field conditions are f=100 Hz, Eac=30 V/cm, and Edc=0 V/cm. In FIG. 6B, the field conditions are changed to f=0 Hz, Eac—300 V/cm, and Edc=0 V/cm. DNA 180 is released from electrode 18 and diffuses away in the direction of the arrows. This process can be repeated indefinitely to trap and release the DNA.

Figure 7A:
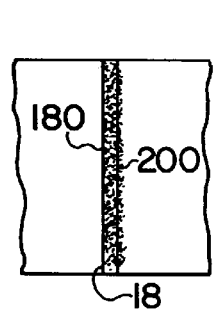
FIG. 7 shows an example of how DNA is trapped (FIG. 7A) and separated FIG. (7B).
Figure 7B:
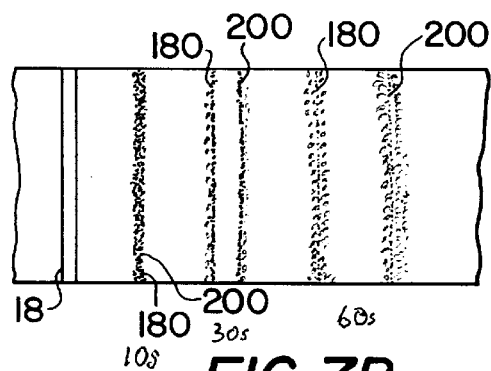

FIG. 7 shows a cartoon of a video demonstration of trapping and launching DNA. In FIG. 7A, T4 DNA 180 and λ DNA 200 are trapped on the trapping electrode 18 by a dielectrophoretic field with f=100–150 Hz, Eac=30 V/cm, and Edc—0. This defines time zero. In FIG. 7B, the DNAs 180 and 200 are launched off the trapping wire 18 into the channel 16 by an electrophoretic field with f=0 Hz, Eac=0 V/cm, and Edc=5 V/cm. After 10 seconds, the DNAs 180 and 200 have not detectably separated. After 30 seconds, the DNAs have migrated at detectably different rates, with λ DNA 200 migrating faster. After 1 minute, the DNAs continue to migrate at different rates through the channel, producing separate bands 180 and 200 clearly visible in the microscope, and broader and more diffuse.

Figure 8:
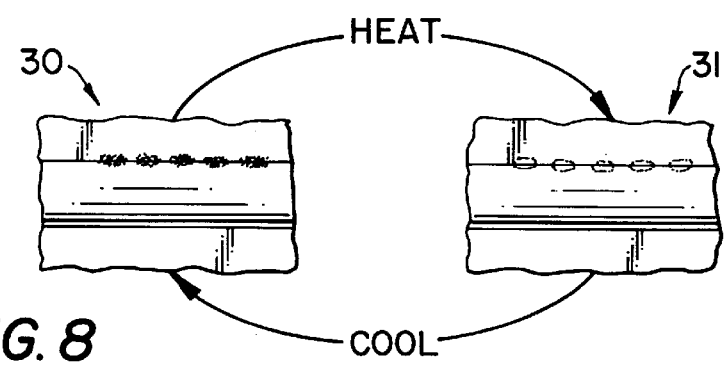
FIG. 8 shows DNA denaturation and renaturation upon heating and cooling of the collector electrode to provide thermal cycling of DNA between cool state and heated state.

FIG. 8 depicts thermal cycling of trapped Hind III digested λ DNA 122. In the cool state 30, TOTO-1 labeled DNA 122 is trapped on a Pt wire 18, with the temperature of the wire being 50° C. Since TOTO-1 only binds to double-stranded DNA when the DNA is double stranded, it fluoresces with this dye. In heated state 31, the temperature of the wire 18 is raised to 90° C., causing the DNA 122 to denature. The fluorescence image disappears. Upon removal of the heating current, the device cools to cool state 30, wire 18 resumes 50° C., and fluorescence of the DNA 122 returns.

In a prototype device, each PCR cycle takes about 1 min, and 20 cycles takes about 20 min. plus trapping and fractionation/sequencing, for a total time of about 25 min. The inventive device can be ultrafast because the AC field helps mixing be much more efficient. In contrast, a very rapid commercial thermocycler (Hybaid, PCR Express) takes 50 min. for 20 cycles. It takes another hour for preparing a gel run. The fastest PCR on a chip, a flow-through PCR, (Kopp et al., Science 280:1046–1048, 1998) takes about 20 min for 20 cycles with a flow rate of 73 nL/s. It also needs a separate gel run for the PCR product, and the required volume is ~90 µl (1200 sec.×73 nl/sec). In the inventive device, for a 1 cm long, 100 µm wide and 1 µm high channel, it takes only 1 nL PCR mixture. Further economies in time and reagents are realized because of the integrated fractionation/sequencing steps.

EXAMPLE 1

Device Fabrication

3" single-crystal quartz (silicone dioxide, $SiO_2$) wafers were used as substrates. 1000 Å PECVD (Plasma Enhanced Chemical Vapor Deposition) $SiO_2$ was deposited on quartz wafers to enhance the adhesion of photoresist on the quartz surface. Shipley 1813 photoresist was then spun on at 4000 rpm for 60 seconds. After baking, the substrate was UV-exposed to a mask which defines the wires and contact pads. The exposed substrate is then moved to a pressurized oven for ammonia ($NH_3$) baking at 80° C. for 84 minutes. (This baking is necessary for reversing the positive tone of photoresist and leaving an undercut of the pattern for facilitating the lift-off process). The imager-reversed substrate was then UV exposed again, without mask, for 60 seconds. Once exposed, the substrate was developed in Microposit MF-321 developer for 1 minute, rinsed with 18MΩ deionized water, and dried with dry nitrogen. After resist de-scum, the substrate was placed in an electron-gun evaporator for platinum (Pt) evaporation. All Pt evaporations took place at pressures below $2 \times 10^{-6}$ Torr and at temperatures below 35° C. A 50–100 Å adhesion layer of titanium (Ti) was first deposited and then 500–1000 Å Pt. After metal evaporation, the wafer was placed in Microposit 1165 resist remover or in acetone for liftoff of excess Pt and Ti. The Pt trapping wires are typically 10 µm wide and 2 cm long with contact pads for electrical connections. The supports, which define the microfluidic channels, were fabricated on the Pt-deposited wafers using photolithography. Multiple channels in parallel made by this method were 0.6 mm wide; other channel widths which allow for capillary action are also suitable. So far, we have developed two ways to define the supports. First, Shipley 1813 resist is spun on the sample at 4000 rpm for 60 seconds. (The channel depth is varied by using different speed for spinning). The sample is then baked on a vacuum hot plate for one minute at 115° C. (or alternatively in an oven for 30 minutes). It is then UV-exposed with a mask and developed with 1:1 Microposit MF-312 developer: 18MΩ deionized water for 1–2 minutes. The sample is dried with dry nitrogen. Hence the supports are defined by resist. Second, polyimide is spun on the sample at 2000 rpm for 50 seconds. The sample is then baked in an oven at 90° C. for 30 minutes, 175° C. for 15 minutes, and 200° C. for 15 minutes. After this 3-step baking, the sample is spun on a Shipley 1813 resist at 4000 rpm for 60 seconds. The sample is baked on the vacuum hot plate at 115° C. for 60 seconds. It is then UV-exposed with a mask and developed with 1:1 Microposit MF-312 developer: 18MΩ deionized water for 1–2 minutes. The sample is dried with dry nitrogen. Now the resist is serving as an etch mask for polyimide. By using reactive ion etcher to etch through the polyimide down to the Pt wire, and using acetone to strip off the residual resist, the supports are defined by polyimide. Besides the above two ways to define supports, PEVCD $SiO_2$ is also preferable. As an example, a 3" quartz wafer fabricated by the above procedures contains 50 10 µm-wide Pt wires and 16 parallel channels. There are no intrinsic difficulties in fabricating 96 parallel channels to accommodate the commercial 96-post pipettors. The number of channels fabricated by this method is limited principally by the width of available wafers and the width of the channel and supports.

Sealing Process

To seal the samples, RTV silicone was prepared: 10:1 ratio of RTV 165A (GE): RTV 165B (GE) wis mixed and then placed in a vacuum chamber. The mixture was pumped for 20–30 minutes at 25° C. for degasing and then spin-coated onto a microscope coverslide (No. 1 or No. 1.5) at 4000 rpm for 1 minute. The coverslip was then baked for about 10 hours at 80° C. in order to cure the RTV. The coverslip was cut to the desired size using a diamond scribe. It was then used to seal the sample channel (RTV-side against the resist posts that define the channel). Before sealing, the surface property of RTV (hydrophobic) may be modified by oxygen plasma treatment for 1–2 minutes. This makes the RTV surface hydrophilic and enhances wettibility.

EXAMPLE 2

DNA preparation

A variety of single-stranded and double-stranded DNAs have been used, for example: fluorescein-labeled 50-mers, TOTO-1 labeled bacteriophage T4, and HindIII digested λ DNA (Sigma and New England Biolabs). T4 is 167 Kbp long, λ is 48 kbp long, and HindIII digested λ has fragments of 23130, 9416, 6557, 4361, 2322, 2027, 564 and 125 bp. All DNA solutions were diluted to 0.25 µg/ml with 0.1 M DTT (a reducing agent), 5 µM TOTO-1 dye, 0.1% POP-6 (Perkin-Elmer), an electrosmosis suppressing agent, and 1/2X TBE buffer (5X: 54 g Tris base, 27.5 g boric acid, and 20 ml 0.5M EDTA, pH 8.0 dissolved in 980 ml deionized water to make 1 liter). DNA was pipetted onto one end of the open channel of the sealed device and capillary action was used to wet the channel with DNA.

EXAMPLE 3

Measurement Apparatus

FIG. 5 depicts the measurement apparatus in relation to the sample. An argon laser which emits a wavelength of 488 nm was used to excite the TOTO-1 dye, thus generating a flourescence image of the DNA, which was directed to a silicon intensified target (S.I.T) camera, a Picture-in-Picture device, and additional imaging equipment. The location of the DNA was observed on the TV monitor. Data processing equipment was used to calculate time and voltage at various points in the device, and can be used to calculate dielectric response of DNA and to obtain other information about the sample.

The position of the DNA may be controlled manually by means of the switches on the control box. Manipulation may also be accomplished automatically.

An AC field from a signal generator is applied for DNA focusing on a Pt wire. As shown in FIG. 4, a direct current voltage was applied across the Pt wire to heat the wire to the melting temperature of ds DNA (90–95° C.). This permits primer and enzymes in the buffer to copy the complementary sequence along the ssDNA.

Since Pt is a very good resistance-temperature detector, temperature taken at the trapping electrode is monitored by the resistance of the platinum wire which is taken from the ratio of V/I across the wire. In this sense, the Pt wire serves not only as a heating source but also as an in-situ thermometer. From the pre-calibrated resistance-temperature curve, we can read the temperature at the wire from its resistance. The resistor box with resistors A and B serves as a current modulator, thus a temperature modulator, through the Pt wire. In turn, it changes the temperature at the wire. Temperature control may be improved by using a Peltier element, a thermoelectric module, for increased speed, $\Delta T/\Delta t$, and by PID control for well controlled temperature. When resistors A 76 and B 78 are open, full current goes through the wire, hence T=90° C. at the wire. When A is closed, less current goes through the wire, thus temperature reduces to 70° C. for extension of the copied dsDNA. When both A and B are closed, the least current runs through the wire, and reduces the temperature to 55° C. for annealing. This completes a thermal cycle of DNA duplication. By repeating the thermal cycling (computer controlled) for 20 cycles, we get an amplification yield on factor of about $2^{20}$ or about $10^6$. Due to the electrodynamic focusing of DNA on the Pt wire, after amplification of different sizes of DNA is done, it is possible to analyze the DNA directly upon launching from the trapping electrode. In this embodiment, the invention provides an integrated DNA amplification and sequencing device.

EXAMPLE 4

Discrete regions of DNA or RNA by reverse transcriptase PCR can be amplified directly on the floating electrode wire by thermocycling (PCR). A typical PCR reaction mixture contains buffer, thermostable DNA polymerase, template DNA (as little as a single molecule), and appropriate pairs of oligonucleotide primers (see, for example, Saiki R K, Gelfand D H, Stoffel S, Scharf S J, Higuchi R, Horn G T, Mullis K B, Erlich H A, "Primer-directed enzymatic amplification of DNA with a thermostable DNA polymerase," Science 239(4839):487–91. (1988)). Template, and then reaction product, is trapped by the dielectrophoretic field on the wire as the thermocycling reaction is carried out. The method of detection uses a fluor that fluoresces strongly only when bound to the double stranded DNA product, shows little or no auto fluorescence when not bound to DNA, and does not inhibit the DNA polymerase chain reaction. One such fluor now in use in this laboratory is SYBR® Green-1 (Molecular Probes) added to the PCR reaction mix at a dilution of 1:40,00–1:100,000. Thus only the polymerase chain reaction product is detected.

The brightness of the image reflects the amount of DNA, and brightness is used to gauge when the thermocycling reaction is over. At that point the product is launched from the wire into the appropriate separation matrix for accurate sizing—cross-linked polyacrylamide for low molecular weight samples, linear acrylamide and polyethylene oxides for larger sizes. This technology can be combined with the array technology described in Austin et al., U.S. Pat. No. 5,427,663, so that the thermocycling reaction is integrated into a chip fabricated in such a manner that the reaction products can be launched directly into the separation medium. Other labeling alternatives that depend for their efficacy on the incorporation of reporter groups into the product can also be used, as reviewed in Wittwer CT et al. (1997), "Continuous fluorescence monitoring of rapid cycle DNA amplification," Biotechniques 22(1):130–138. The methods described here are useful for multiplex genotyping, diagnostics, forensics, reverse transcriptase PCR, quantitative PCR, and sizing PCR products from a variety of sources. See, for example, Ju et al., (1995), "Fluorescence energy transfer dye-labeled primers for DNA sequencing and analysis," Proc Natl Acad Sci USA, 92(10):4347–51; Glazer et al. (1997), "Energy-transfer fluorescent reagents for DNA analyses," Curr. Opin Biotechnol, 8(1):94–102.

The dye could be used to calibrate parameters for the reaction, and then left out in actual cycling steps, but it is preferable to use the dye as a monitoring tool. Preferred dyes are large groove binding dyes that do not bind to single stranded DNA, have low or no autofluorescence, and do not interfere with PCR.

Alternatively, this device can be used for the amplification scheme called "strand displacement amplification" (Walker, GT PCR Methods and Applications 1993 3: 1–6.). In this method DNA template, buffer, deoxytriphosphates, DNA polymerase, primers and a restriction endonuclease are incubated at an elevated temperature and the DNA is amplified linearly by strand displacement. The product is detected as described above prior to launching, fractionation, and detection, or the reaction may be followed by fluorescence polarization (Spears P A, Linn C P, Woodard D L, Walker G T Anal Biochem 1997 247:130–137).

EXAMPLE 5

DNA sequencing is typically carried out using single or double-stranded templates by the linear polymerase chain reaction, so-called "cycle sequencing". Murray (1989), "Improved double-stranded DNA sequencing using linear polymerase chain reaction," Nucl. Acid Res. 17:8889; Craxton (1991), "Linear amplification sequencing: A powerful method for sequencing DNA," Methods: A companion to Methods in Enzymology, 3:20–26. In a typical reaction, buffer, thermostable DNA polymerase, template, and an oligonucleotide primer specific for only one strand of the template are combined with deoxyribonucleoside triphosphates and their dideoxynucleoside derivatives. The reaction is then subjected to many rounds of thermocycling and the reaction products are separated on a sequencing gel. Slatko (1994), "Thermal cycle dideoxy DNA sequencing," Methods Mol Biol 31:35–45. According to the invention, the entire "cycle sequencing" reaction is carried out on template trapped on the dielectrophoretic floating electrode, and the reaction products are launched directly into a downstream separation matrix, such as a sequencing gel or array as described above. Here, as elsewhere, the dideoxy chain terminators can be labeled with fluorescent dyes so that all 4 bases can be identified (see, for example, DNA Sequencing. Chemistry Guide (1995) Perkin Elmer part number 903563). Alternatively methods now known or hereafter discovered may also be used, such as resonance energy transfer-labeled fluorescent primers can be used. Ju J., et al. Anal. Biochem. (1995).

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A device for manipulating polyelectrolytes, comprising:
   (a) a microfluidic channel dimensioned to accommodate the polyelectrolytes in a fluid,
   (b) field electrodes positioned to provide a dielectrophoretic field in the channel,
   (c) a single trapping electrode positioned in the channel between the field electrodes, the field electrodes and trapping electrode being capable of fluid and electrical communication with each other via the channel,
   such that when the polyelectrolyte in the fluid is applied to the device, the polyectrolyte can be (i) trapped on the single trapping electrode by the dielectrophoretic field, (ii) heated by current applied to the trapping electrode, and (iii) released when the dielectrophoretic field is not applied.

2. The device of claim 1, further comprising a matrix in the channel downstream from the trapping electrode capable of fractionating and/or analyzing the polyelectrolytes released from the collecting electrode.

3. The device of claim 1, further comprising imaging equipment to visualize the polyelectrolytes.

4. The device of claim 1, wherein said channels have dimensions in the range of about 0.1 to about 100 $\mu$m in height, about 1 to about 1000 $\mu$m in width, and about 1 to about 10 cm in length.

5. The device of claim 1, wherein the trapping electrode has dimensions in the range of about 10 to about 100 nm in height, about 10 nm to about 20 $\mu$m in width, and about 1 $\mu$m to about 2 cm in length.

6. The device of claim 1, wherein the field electrodes have dimensions in the range of about 10 $\mu$m to about 1 mm in height, about 10 $\mu$m to about 1 cm in width, and about 100 $\mu$m to about 10 cm in length.

7. The device of claim 1, wherein the alternating current has a frequency up to about 10 MHZ, a voltage up to about 1000 V/cm.

8. The device of claim 1, wherein there are a plurality of parallel channels arranged on the substrate.

9. The device of claim 1, wherein the substrate is a quartz or silicon chip.

10. The device of claim 1, wherein the further comprising an alternating current source for the field electrodes and a current source for the trapping electrode.

11. The device of claim 10, wherein the current source for the trapping electrode comprise circuitry to control and measure heating.

12. The device of claim 1, wherein the trapping electrode is made of platinum.

13. The device of claim 1, wherein the polyelectrolyte is a nucleic acid.

14. The device of claim 1, wherein the substrate comprises a material selected from the group consisting of SiO2, polyimide, p-xylylene, PDMS or PMMA.

15. The device of claim 1, wherein the channel is covered with a seal comprising a coverslip and a sealant gasket.

16. A method for thermal cycling and harvesting of a polyelectrolyte comprising:
   (a) placing the polyelectrolyte in a fluid in a microfluidic channel having a trapping electrode,
   (b) reversibly trapping the polyelectrolyte on the trapping electrode by applying a dielectrophoretic field to the channel, and
   (c) heating the polyelectrolyte on the trapping electrode.

17. The method of claim 16, wherein the step of heating the polyelectrolyte comprises applying a current to the trapping electrode.

18. The method of claim 17, further comprising reducing the current and allowing the nucleic acid to renature.

19. The method of claim 17, wherein the polyelectrolyte is a nucleic acid, and heating denatures the nucleic acid.

20. The method of claim 19, further comprising releasing the polyelectrolyte by removing the dielectrophoretic field and separating, sequencing, and/or analyzing the polyelectrolyte.

21. The method of claim 19, further comprising determining the sequence of the nucleic acid by reacting the trapped nucleic acid with amplification reagents, allowing nucleic acid amplification to occur, releasing the polyelectrolyte by removing the dielectrophoretic field, fractionating the nucleic acid, and scanning the fractions.

22. The method of claim 21, wherein a plurality of samples are processed simultaneously in separate channels.

23. The method of claim 22, wherein the dielectrophoretic field is produced by field electrodes that also produce an electrophoretic field for fractionating the nucleic acid.

24. The method of claim 21, further comprising fractionating the released polyelectrolyte.

25. A device for manipulating polyelectrolytes, comprising:
   (a) microfluidic means for microfluidically accommodating a polyelectrolyte in a fluid,
   (b) means for controllably providing a dielectrophoretic field within the microfluidic means,
   (c) trapping means comprising a trapping electrode on which the polyelectrolyte is trapped in the presence of the dielectrophoretic field, and
   (d) means for intrinsically heating the trapping means.

26. The device according to claim 25, further comprising means for in-situ temperature measurement using the trapping means as a sensor.

27. The device of claim 25 further comprising means for fractionating and/or analyzing the polyelectrolyte.

28. A method for thermal cycling of a polyelectrolyte in a fluid in a microfluidic channel having a trapping electrode, comprising:
   (a) a step for trapping the polyelectrolyte on the trapping electrode,
   (b) a step for heating the polyelectrolyte with the trapping electrode, and
   (c) a step for releasing the polyelectrolyte.

* * * * *

UNITED STATES PATENT AND TRADEMARK OFFICE
CERTIFICATE OF CORRECTION

PATENT NO. : 6,203,683 B1
DATED : March 20, 2001
INVENTOR(S) : Austin et al.

Page 1 of 1

It is certified that error appears in the above-identified patent and that said Letters Patent is hereby corrected as shown below:

In the bibliograghic information, add the following statement regarding FEDERALLY SUPPORTED RESEARCH AND DEVELOPMENT:

STATEMENT REGARDING FEDERALLY SUPPORTED
RESEARCH AND DEVELOPMENT

This work was supported in part by grants awarded by the National Institutes of Health, Grant Nos. - HG01506 and 5 RO1 GM55453-01, and the U.S. Government may therefore have certain rights in this invention.

Signed and Sealed this

Twenty-sixth Day of February, 2002

Attest:

Attesting Officer

JAMES E. ROGAN
Director of the United States Patent and Trademark Office